United States Patent [19] Pearson

[11] Patent Number: 4,589,879

[45] Date of Patent: May 20, 1986

[54] CANNULA ASSEMBLY HAVING CLOSED, PRESSURE-REMOVABLE PIERCING TIP

[75] Inventor: Stephen Pearson, Ingleside, Ill.

[73] Assignee: Baxter Travenol Laboratories, Inc., Deerfield, Ill.

[21] Appl. No.: 548,796

[22] Filed: Nov. 4, 1983

[51] Int. Cl.[4] .......................... A61B 19/00; A61M 5/32; A61M 37/00

[52] U.S. Cl. .......................... 604/411; 604/88; 604/410; 604/414; 604/416

[58] Field of Search .............. 604/411, 416, 56, 86–90, 604/130, 236–238, 272, 274

[56] References Cited

U.S. PATENT DOCUMENTS

| | | | |
|---|---|---|---|
| 1,008,128 | 11/1911 | Flagg . | |
| 2,178,840 | 11/1939 | Lorenian . | |
| 3,205,889 | 9/1965 | Alder et al. | 604/262 |
| 3,396,660 | 8/1968 | Bilson et al. . | |
| 3,457,921 | 7/1969 | Waldeisen . | |
| 3,645,268 | 2/1972 | Capote . | |
| 3,861,393 | 1/1975 | Durand . | |
| 3,893,866 | 7/1975 | Hollingsworth . | |
| 3,904,059 | 9/1975 | Bellamy, Jr. et al. . | |
| 3,976,073 | 8/1976 | Quick et al. . | |
| 4,121,586 | 10/1978 | Lawrence et al. | 604/130 |
| 4,153,057 | 5/1979 | Köbel | 604/90 |
| 4,244,364 | 1/1981 | Grushkin | 604/254 |
| 4,340,049 | 7/1982 | Munsch . | |
| 4,405,317 | 9/1983 | Case | 604/90 |
| 4,410,321 | 10/1983 | Pearson et al. . | |
| 4,464,174 | 8/1984 | Ennis | 604/90 |
| 4,467,588 | 8/1984 | Carveth | 604/87 |

*Primary Examiner*—C. Fred Rosenbaum
*Assistant Examiner*—Michelle Lester
*Attorney, Agent, or Firm*—Paul C. Flattery; John P. Kirby, Jr.; Bradford R. L. Price

[57] ABSTRACT

A cannula assembly especially for medical use is disclosed which virtually eliminates coring during the piercing of a barrier. The cannula assembly includes a hollow cylindrical shank and a piercing tip removably mounted in and closing one end of the shank. Pressurized introduction of fluid through the shank forces the piercing tip out of engagement with the shank, placing opposite sides of the barrier in fluid communication.

12 Claims, 8 Drawing Figures

CANNULA ASSEMBLY HAVING CLOSED, PRESSURE-REMOVABLE PIERCING TIP

TECHNICAL FIELD

The present invention relates generally to structure for piercing a barrier and placing both sides of the barrier in fluid communication through the structure, and more particularly relates to a cannula assembly especially adapted for use in the medical field.

BACKGROUND OF THE INVENTION

U.S. Pat. No. 4,410,321 to Pearson, et al. is hereby incorporated by reference.

A large number of drugs are packaged in well known glass drug bottles having rubber-like pierceable rubber stoppers. These drugs are usually in powder, including crystalline, form. For delivery to a patient, the drug must be reconstituted. This is typically performed by piercing the stopper with a hollow stainless steel needle having a sharpened tip. The needle is secured to a syringe assembly of well known construction, including a cylindrical barrel and piston.

Typically, the needle is brought to a point on one side of the needle wall by a bevel structure so that the needle tip is quite sharp. Such needles are subject to coring. Coring is the collection of barrier material, in this case part of the stopper, inside the hollow needle tip. When liquid is pumped between the syringe and the drug vial for drug reconstitution, any stopper material in the needle tip caused by coring results in stopper particulate matter in the liquid.

Particulate matter may also be generated, although to a lesser degree, between the stopper and the outer wall of the needle as the needle passes through the stopper.

Such known needle structures are expensive to manufacture and may require swaging, grinding, buffing and sandblasting operations. Most stainless steel needles also generally require lubrication such as with silicone due to the non-slip characteristics of the stainless steel. Other needle structures are known which have a closed end but which employ openings in the sidewall of the needle. This may somewhat reduce coring but the needle interior is still open during piercing of a barrier.

After the drug is reconstituted in the liquid, which may be sterile water or sterile saline or dextrose solution, for example, the solution is withdrawn from the vial into the syringe for further injection, typically into a patient directly or into a solution container such as a VIAFLEX® container sold by Travenol Laboratories, Inc. of Deerfield, Ill. The VIAFLEX container may be connected to the patient's intravenous system by means of a parenteral solution administration set. If the reconstituted drug is to be injected into a solution container, a reconstitution device such as the vial and syringe connector assembly shown in U.S. Pat. No. 3,976,073 may be employed, in order to pierce an injection site on the solution container. The syringe connector assembly shown in U.S. Pat. No. 3,976,073 also includes a blunt end of the needle opposite from the pointed end, the blunt end being adapted for piercing a specially adapted diaphragm so as to form a flap in the diaphragm to reduce coring.

More recently, a closed drug delivery system utilizing a sterile coupling has been developed, as described in the above-mentioned U.S. Pat. No. 4,410,321, incorporated by reference herein. There, a needle mounted to a flexible, compressible chamber is also secured in pre-piercing relation to a standard drug vial by a junction means which may comprise a block of injection molded plastic around both the rubber stopper and the needle. To place the flexible chamber and the vial in fluid communication, the plastic junction, as well as the rubber stopper of the vial is pierced, thereby making coring and the generation of particulate matter a possibility with the plastic junction means as well as with the rubber stopper in the vial.

It would be desirable to employ a needle construction, both with the junction means and vial combination shown in U.S. Pat. No. 4.410,321, as well as with the rubber stopper of a standard drug vial, which both eliminates coring and reduces the generation of particulate matter.

SUMMARY OF THE INVENTION

The present invention is directed to a functionally superior cannula assembly which eliminates or virtually eliminates coring. The cannula assembly reduces the generation of particulate matter in the reconstitution solution. Further, the cannula assembly of the invention enables the use of a larger gauge cannula to permit faster fluid flow therethrough. The cannula assembly is less expensive to manufacture than known steel-pointed needles.

The cannula assembly comprises a hollow shank and a piercing tip removably mounted in one end of the shank. The cannula assembly of the invention is closed at one end with the piercing tip. The piercing tip of the assembly, while still mounted to the shank, may be urged through a barrier such as a rubber stopper in a drug vial. The pressurized introduction of fluid through the shank from a compressible chamber attached to the other end of the shank generates enough force to disengage the piercing tip from the shank, placing the compressible chamber and the opposite side of the barrier, such as the vial contents, in open communication.

DETAILED DESCRIPTION OF THE PREFERRED EMBODIMENTS

Figure 1:
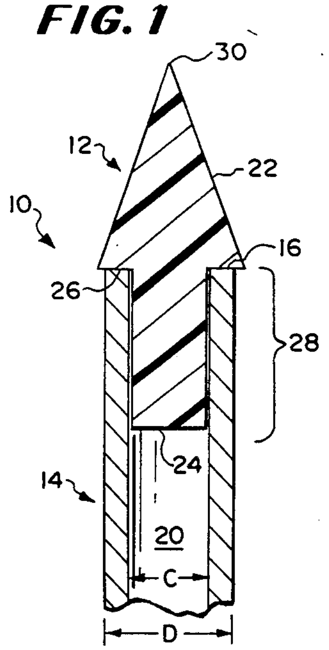
FIG. 1 is a fragmentary, cross-sectional view of the cannula assembly.
Figure 2:
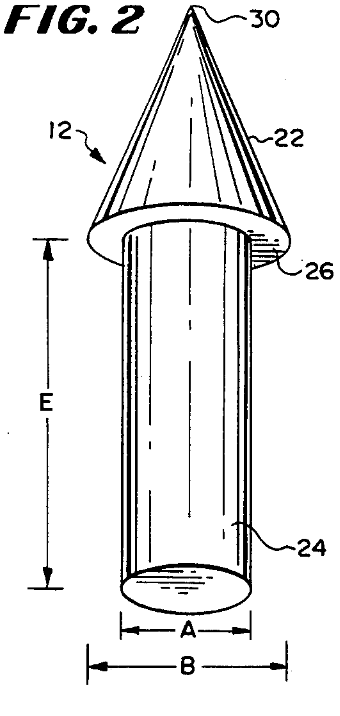
FIG. 2 is a perspective view of the piercing tip.
Figure 5:
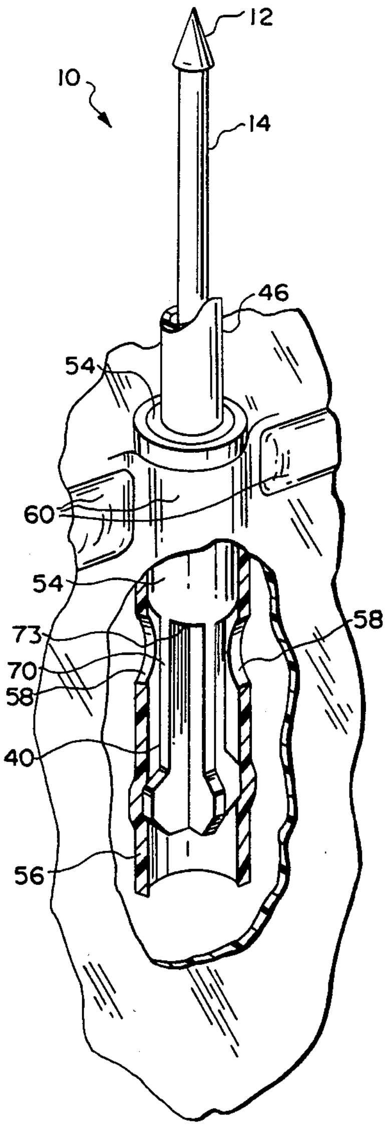
FIG. 5 is an enlarged, partially cutaway view of the cannula assembly.

As seen in FIGS. 1, 2 and 5, the cannula assembly 10 of the present invention includes a piercing tip 12 and a hollow shank 14. The hollow shank 14 includes first and second ends 16, 18, respectively. The hollow shank 14 may be made of any substantially rigid material but when employed for medical use must be made of a medical quality material such as stainless steel. The first end 16 of the shank 14 is a blunt, flat end. The second end 18 is also flat in the preferred embodiment.

The piercing tip 12 is preferably solid and is mounted to the first end 16 to effectively close the shank interior 20 at the first end 16. The piercing tip 12 preferably includes a conical portion 22 and a cylindrical portion 24 integral with the conical portion 22 and extending from the base 26 of the conical portion 22. The diameter A of the cylindrical portion is preferably less than the diameter B of the base 26. The diameter of the cylindrical portion 24 is sized to be somewhat smaller than the interior diameter C of the shank 14. The base 26 of the conical portion 22 rests atop the first end 16 of the shank 14. The piercing tip 12 thus rests loosely within the first end portion 28 of the shank 14.

The piercing apex 30 of the conical portion 22 is sufficiently sharp to pierce a barrier such as the rubber-like stopper of a drug vial. In the preferred embodiment, the piercing apex 30 is defined by an angle of about fifteen degrees. Preferably the piercing apex 30 is not substantially greater than 60°.

The diameter B of the base 26 is preferably slightly larger than the outside diameter D of the shank 14. While it is believed that the cannula assembly will function adequately when the diameter of the base 26 is equal to or slightly less than the outer diameter of the shank 14, a base diameter B slightly larger than the shank outer diameter D is believed to reduce drag between the shank 14 and barrier during piercing of the barrier.

The length E of the cylindrical portion 24 is not critical but should be long enough to aid in keeping the piercing tip 12 within the shank 14.

Table 1 gives various dimensions for three sizes of shank and piercing tip for the cannula assembly. Table 1 is meant for illustration purposes only and is not intended to limit the scope of the present invention.

TABLE 1

CANNULA ASSEMBLY DIMENSIONS (inches and centimeters)

| Piercing Tip | | | Shank | |
|---|---|---|---|---|
| A | B | E | C | D |
| Example 1: | | | | |
| 0.055/0.140 | 0.075/0.191 | 0.150/0.381 | 0.058/0.147 | 0.070/0.178 |
| Example 2: | | | | |
| 0.070/0.178 | 0.090/0.229 | 0.180/0.457 | 0.065/0.165 | 0.083/0.211 |
| Example 3: | | | | |
| 0.110/0.279 | 0.180/0.457 | 0.360/0.914 | 0.120/0.305 | 0.160/0.406 |

The piercing tip 12 must be made of a relatively hard material and must be a medical grade material when employed with medical substances. For medical applications, the piercing tip 12 may, for example, be an acrylic such as a polycarbonate, or LEXAN TM, made by General Electric. The piercing tip 12 may also be made of nylon. The piercing tip 12 may ideally be made of an even harder material such as stainless steel, but a plastic piercing tip has been found to work very well without the expensive material and manufacturing costs of a stainless steel tip. Furthermore, while most stainless steel needles require the post-forming addition of a lubricant, the plastic material forming the piercing tip 12 may be inherently lubricious.

Figure 3:
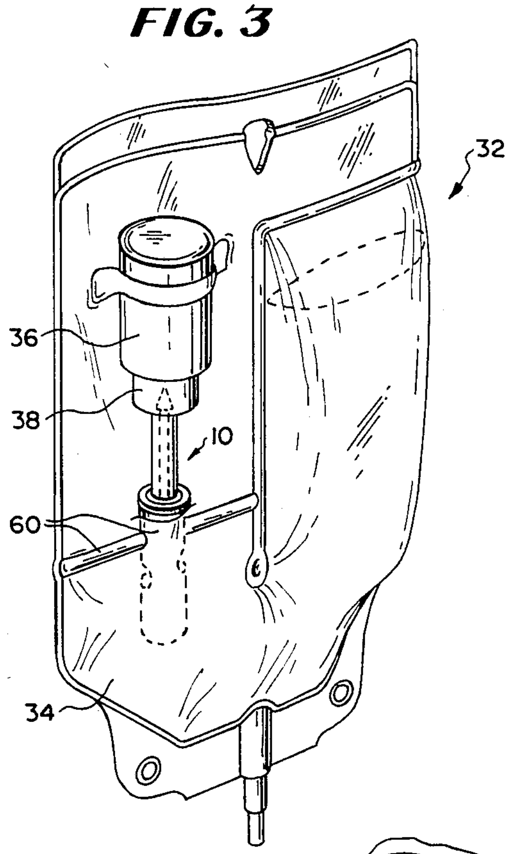
FIG. 3 is a perspective view of the cannula assembly mounted to a compressible chamber and maintained in predetermined spatial relation to a drug vial by positioning means.
Figure 4:
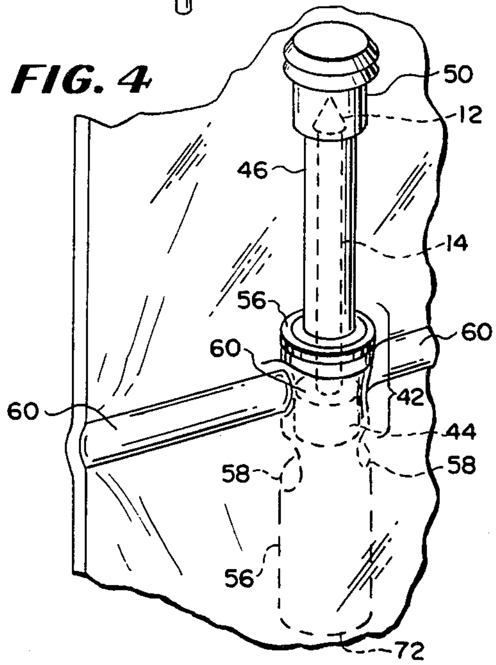
FIG. 4 is a fragmentary, perspective view of the cannula assembly shown in FIG. 3.

In the preferred embodiment, the cannula assembly 10 is utilized in the closed drug delivery system 32 seen in FIGS. 3 through 8 and described in detail in U.S. Pat. No. 4,410,321. Referring to FIGS. 3 through 5, the drug delivery system 32 includes a compressible chamber 34 and a drug vial 36, secured together by junction means 38 comprising a block of plastic material surrounding the access means to both the compressible chamber 34 and the vial 36.

The cannula assembly 10 is mounted to and may include the compressible chamber 34 and valve means such as a frangible closure 40. The frangible closure 40 may be of the type described in U.S. Pat. No. 4,340,049, including a hollow tubular portion 54, breakaway stem 70 and a frangible portion 73 intermediate the tubular portion 54 and the stem 70.

The second end portion 42 of the shank 14 is mounted within a plastic needle hub 44. The piercing tip 12, shank 14 and needle hub 44 are mounted within a flexible plastic sleeve 46. The sleeve 46 may be bonded at its first end 48 to the needle hub 44 by conventional means such as solvent bonding. A pierceable plastic membrane 50 is secured to the second end 52 of the sleeve 46 and encloses the piercing tip 12 and the first end portion 28 of the shank 14. The shank second end portion 42, the needle hub 44 and the sleeve 46 are mounted in the hollow tubular portion 54 of the frangible closure 40. The frangible closure 40 is mounted in a hollow retaining member 56 which may also include side ports 58. The hollow retaining member 56 and therefore the cannula assembly 10 are secured between the sheets of the compressible chamber 34 at a heat seal 60.

Figure 6:
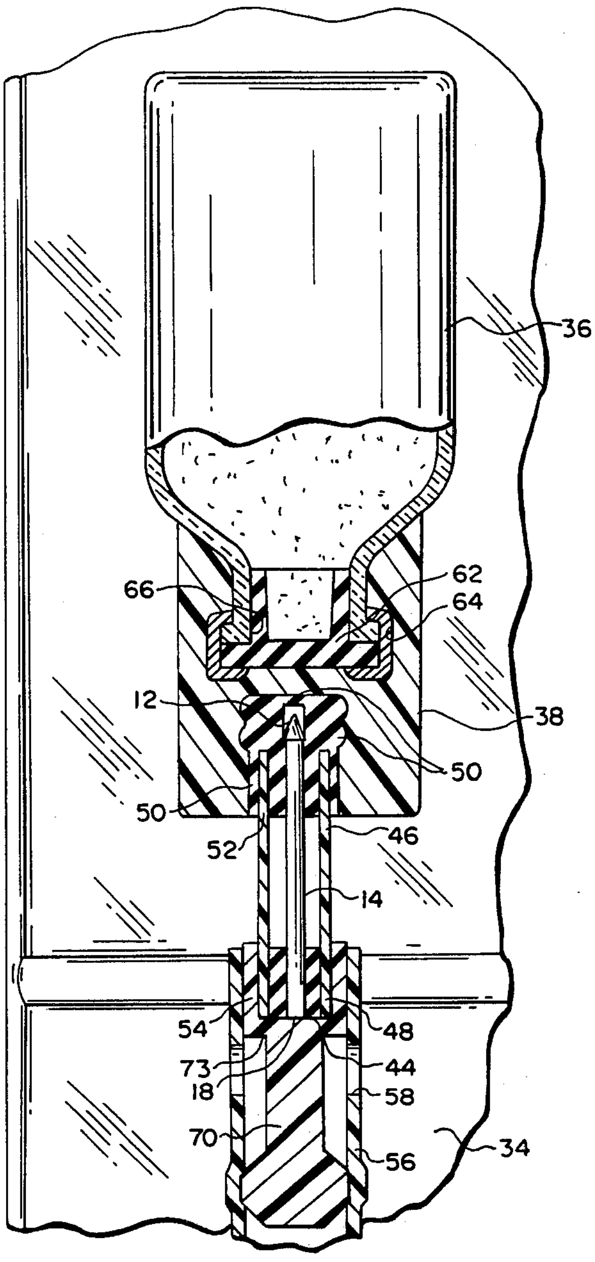
FIG. 6 is a cross-sectional view of the cannula assembly and positioning means.

Referring to FIG. 6, it is seen that the junction means 38 keeps the cannula assembly 10 in specific relation to the rubber stopper 62 of the drug vial 36. Typically, a metal band 64 surrounds the outer periphery of the vial neck 66 and the stopper 62.

Figure 7:
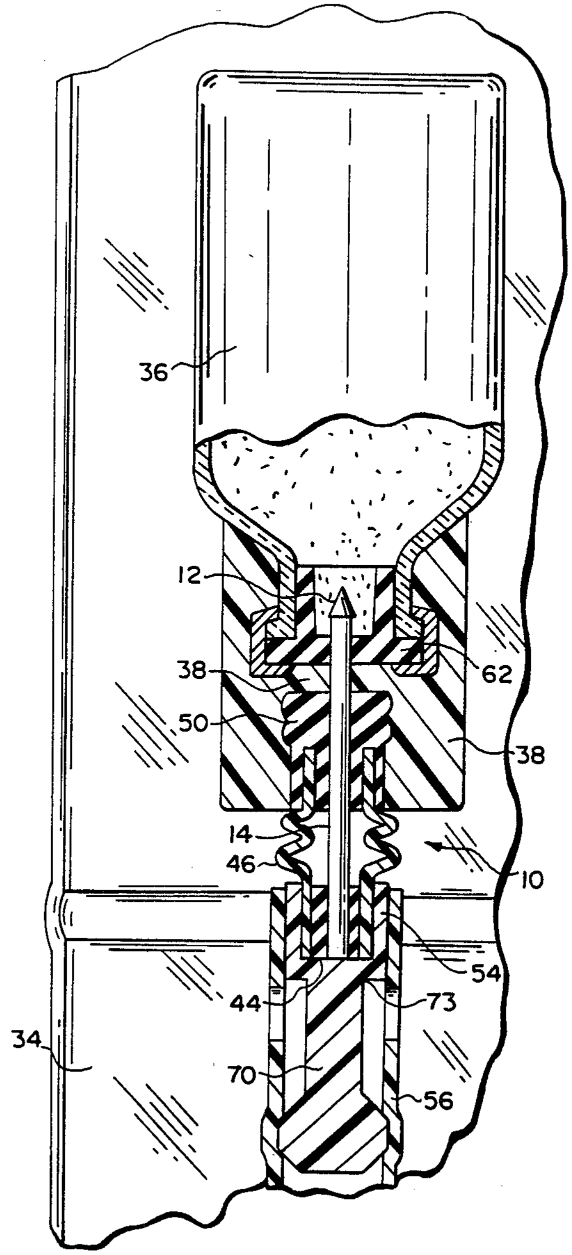
FIG. 7 is a view similar to FIG. 6 illustrating operation of the cannula assembly.
Figure 8:
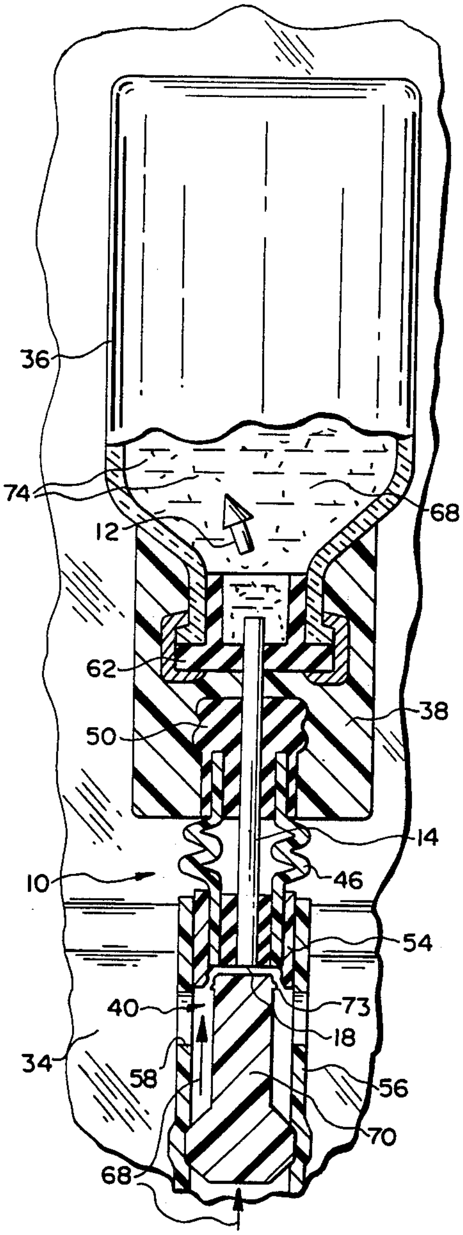
FIG. 8 is a view similar to FIG. 7, further illustrating operation of the cannula assembly.

Operation of the cannula assembly is best illustrated in FIGS. 7 and 8. The compressible chamber 34 and vial 36 are placed in communication by grasping the hollow retaining member 56, for example, from the outside of the chamber 34 and urging the cannula assembly 10 into the vial 36. The sleeve 46 collapses to allow for this movement. As seen in FIGS. 6 and 7, the piercing tip 12 of the cannula assembly 10 pierces the plastic membrane 50, the plastic junction means 38 and the rubber stopper 62 in order to gain access to the vial. Since the piercing tip 12 completely closes the shank 14. there is no coring. Stated differently, no particulate matter from the membrane, junction means or stopper enters the hollow shank 14.

Once the piercing tip 12 and the first end portion 28 of the cannula assembly 10 are within the drug vial 36, the frangible closure 40 is broken at the frangible portion 73, as seen in FIG. 8. This allows fluid 68 such as dextrose solution, stored in the compressible chamber 34, to enter the shank interior 20 through the shank second end 18. The second shank end 18 is defined by that portion of the shank 14 where fluid may enter, other than the first shank end 16. Fluid may flow into the shank interior 20 around the breakaway stem 70 through the retaining member end 72, side ports 58 and hollow tubular portion 54.

Finally, the compressible chamber 34 is compressed by simply squeezing the chamber 34. This pressure is enough to force the piercing tip 12 out of engagement with the shank 14 and into the vial 36. Fluid 68 flows from the chamber 34 into the vial 36. The drug 74 in the vial 36 may now be reconstituted with the fluid 68 and delivered through the shank 14 into the compressible chamber 34, for subsequent delivery to a patient. The piercing tip 12 remains within the vial 36.

The cannula assembly 10 prevents or at least virtually prevents any particulate matter whatsoever from entering the hollow shank, which particulate matter could subsequently be mixed into the fluid 68.

As discussed above, the base 26 preferably has a diameter slightly greater than the outer diameter of the shank 14. Although this provides a wider cross-section which must be urged through the various barrier elements, it is believed that piercing is actually easier with the enlarged base 26 because the greater base diameter reduces drag, or frictional forces, between the shank 14 and the barrier members 50, 38, 62. The cannula assembly 10 also creates little, if any, particulate matter out of the barrier material as the outer surfaces of the tip 12 and shank 14 pierce the barrier members.

While the cannula assembly 10 has been particularly described with reference to the closed drug delivery system 32 utilizing the junction means 38, the cannula assembly 10 may be used with other structure. For example, positioning means other than the junction means 38 may be employed in order to hold the cannula assembly 10 in a particular pre-piercing relation to a barrier. The positioning means may be structure attached to the outside of the chamber 34 and the vial 36 to hold the vial and the chamber in fixed, spaced relation without itself forming part of the barrier to be pierced. However, the positioning means may still aid in maintaining the piercing tip 12 within the first end portion 28 of the hollow shank 14. In the embodiment described in detail above, maintenance of the piercing tip 12 within the shank 14 is assured by the sleeve 46 and membrane 50 structure closely surrounding the piercing tip 12.

It may also be possible to employ the cannula assembly 10 of the invention without any overlying structure such as the sleeve and membrane or any positioning means such as the junction means 38. In such a case however, the piercing tip would need to be securely mounted within the shank 14 such as by way of a close friction fit between the cylindrical portion 24 and the interior diameter C of the shank. This would require the use of higher pressure force to disengage the tip from the shank after a vial stopper is pierced.

Also, the compressible chamber need not be a flexible walled chamber but may instead include other structure such as a syringe.

Another advantage of the cannula assembly 10 is that it provides a positive indication that the stopper in the vial has been pierced because the piercing tip 12 remains in the vial once it is accessed. Further, in the embodiment where a syringe is used and no positioning means is employed, the cannula structure is a tamper indicator because use of the cannula assembly necessarily removes the piercing tip.

From the above, it is seen that the cannula assembly 10 of the invention virtually eliminates coring and the generation of any particulate matter caused by piercing a barrier. This prevention of particulate matter generation is especially important in medical applications. Elimination of the coring problem allows a much larger shank to be used, thereby facilitating faster flow rates between two containers after the barrier is pierced. This feature is of great importance where speed is critical or when a large volume of fluid must be transferred.

While various embodiments and features have been described in detail herein and shown in the accompanying drawings it will be evident that various further modifications are possible without departing from the scope of the invention.

What is claimed is:

1. A cannula assembly comprising:

(a) a hollow shank having first and second ends;

(b) a piercing tip for piercing a barrier, removably mounted in and closing off said first shank end, said piercing tip including (i) a substantially conical shaped portion having a base and (ii) a substantially cylindrical portion extending from said base, wherein the diameter of said cylindrical portion is less than the diameter of said base;

(c) said second shank end adapted for the introduction of a fluid into said shank at a pressure high enough to disengage and thereby operatively disassociate said piercing tip from the remainder of said cannula assembly and to force said piercing tip out of said first shank end, said cannula assembly virtually preventing the collection of barrier material inside said hollow shank.

2. The cannula assembly as in claim 1, wherein the diameter of said base of said conical portion is greater than the outer diameter of said hollow shank first end.

3. The cannula assembly as in claim 1, further comprising valve means communicating with said second shank end for the selective introduction of fluid into said shank.

4. The cannula assembly as in claim 3, wherein said valve means comprises a frangible closure.

5. The cannula assembly as in claim 3, further comprising a compressible chamber for holding the fluid, said compressible chamber being fixedly mounted in relation to at least one of said second shank end and said valve means such that upon opening of said valve means fluid in said compressible chamber is in open communication with the interior of said shank.

6. The cannula assembly as in claim 1, further comprising a compressible chamber for holding the fluid, said compressible chamber being fixedly mounted in relation to said second shank end, such that fluid in said chamber may be placed in communication with the interior of said shank.

7. The cannula assembly as in claim 6, wherein said compressible chamber is defined by a flexible wall.

8. The cannula assembly of claim 1, further comprising pierceable barrier positioning means secured adjacent both said hollow shank and the barrier for maintaining said piercing tip in pre-piercing relation to the barrier.

9. The cannula assembly as in claim 8, wherein said positioning means prevents inadvertent removal of said piercing tip from said hollow shank.

10. The cannula assembly as in claim 8, wherein said positioning means includes junction means between said piercing tip and the pierceable barrier, wherein said piercing tip is adapted for piercing said junction means before piercing the barrier.

11. The cannula assembly as in claim 6, further comprising a sleeve mounted about said shank and said peircing tip and a membrane closing said sleeve near said piercing tip, said sleeve and membrane limiting movement of said piercing tip relative to said shank.

12. A method for piercing a barrier utilizing the cannula assembly as in claim 1, to thereby place the interior of the hollow shank into fluid communication with the opposite side of the barrier, the steps comprising:

(a) urging the piercing tip through the barrier, with the piercing tip still secured to the hollow shank;

(b) subsequently introducing fluid into the shank at a pressure great enough for (c) disengaging and thereby operatively disassociating said piercing tip from the remainder of said cannula assembly and forcing the piercing tip out of engagement with the first shank end.

* * * * *